(12) United States Patent
Yasuda et al.

(10) Patent No.: US 8,308,350 B2
(45) Date of Patent: Nov. 13, 2012

(54) METHOD OF DETERMINING THERMAL PROPERTY OF SUBSTRATE AND METHOD OF DECIDING HEAT TREATMENT CONDITION

(75) Inventors: Yoichiro Yasuda, Tokyo (JP); Toshiyuki Tsukamoto, Tokyo (JP); Masamori Sanaka, Tokyo (JP); Hiroshi Asechi, Tokyo (JP); Atsuhiro Ogura, Tokyo (JP)

(73) Assignee: Applied Materials, Inc., Santa Clara, CA (US)

( * ) Notice: Subject to any disclaimer, the term of this patent is extended or adjusted under 35 U.S.C. 154(b) by 1123 days.

(21) Appl. No.: 11/573,257

(22) PCT Filed: Aug. 9, 2005

(86) PCT No.: PCT/JP2005/014577
§ 371 (c)(1),
(2), (4) Date: Jul. 6, 2007

(87) PCT Pub. No.: WO2006/016579
PCT Pub. Date: Feb. 16, 2006

(65) Prior Publication Data
US 2007/0291818 A1    Dec. 20, 2007

(30) Foreign Application Priority Data
Aug. 9, 2004  (JP) ................................ 2004-232584

(51) Int. Cl.
*G01N 25/20*    (2006.01)
*G01K 3/00*     (2006.01)
*G01K 13/00*    (2006.01)
*G01J 5/00*     (2006.01)

(52) U.S. Cl. ........... 374/43; 374/121; 374/141; 374/104

(58) Field of Classification Search ................... 374/141, 374/121, 43, 104
See application file for complete search history.

(56) References Cited

U.S. PATENT DOCUMENTS 5,561,612 A * 10/1996 Thakur ........................ 700/300
(Continued)

FOREIGN PATENT DOCUMENTS
JP  H05-209233 A   8/1993
(Continued)

OTHER PUBLICATIONS

PCT International Search Report mailed Nov. 15, 2005 for PCT Application No. PCT/JP2005/014577.
(Continued)

*Primary Examiner* — Lisa Caputo
*Assistant Examiner* — Mirellys Jagan
(74) *Attorney, Agent, or Firm* — Moser Taboada; Alan Taboada

(57) ABSTRACT

[Problem] To provide a method that can determine a thermal property of a substrate in a short time and a method that can determine a thermal process condition of an open-loop step. [Solving Means] In accordance with the substrate thermal property determining method of the present invention in a rapid thermal processing apparatus 1 comprising lamps 9 for heating a wafer W and temperature sensors T1 to T7 arranged so as to oppose the lamps 9, temperature data sequentially outputted from the temperature sensors T1 to T7 is obtained, while subjecting the wafer W arranged between the lamps 9 and temperature sensors T1 to T7 to pulsed heating with the lamps 9. Thereafter, the thermal property of the wafer W is determined by using the temperature data.

17 Claims, 16 Drawing Sheets

U.S. PATENT DOCUMENTS

| | | | | |
|---|---|---|---|---|
| 5,738,440 A * | 4/1998 | O'Neill et al. | | 374/9 |
| 5,769,540 A * | 6/1998 | Schietinger et al. | | 374/127 |
| 5,993,059 A * | 11/1999 | O'Neill et al. | | 374/126 |
| 6,044,203 A * | 3/2000 | Dawson et al. | | 392/416 |
| 6,056,434 A * | 5/2000 | Champetier | | 374/126 |
| 6,188,050 B1 * | 2/2001 | Duffer et al. | | 219/497 |
| 6,207,936 B1 | 3/2001 | de Waard et al. | | |
| 6,310,327 B1 * | 10/2001 | Moore et al. | | 219/405 |
| 6,329,304 B1 * | 12/2001 | Kuznetsov et al. | | 438/799 |
| 6,864,463 B2 | 3/2005 | Ikeda | | |
| 2002/0080850 A1 * | 6/2002 | Baba | | 374/43 |
| 2002/0189757 A1 * | 12/2002 | Denton et al. | | 156/345.27 |
| 2004/0018008 A1 * | 1/2004 | Koren et al. | | 392/416 |
| 2004/0023418 A1 * | 2/2004 | Hwang | | 438/5 |
| 2004/0149715 A1 * | 8/2004 | Timans et al. | | 219/390 |
| 2005/0063448 A1 * | 3/2005 | Kusuda | | 374/1 |
| 2005/0063453 A1 * | 3/2005 | Camm et al. | | 374/161 |
| 2009/0161724 A1 * | 6/2009 | Timans | | 374/161 |
| 2009/0242543 A1 * | 10/2009 | Nenyei et al. | | 219/412 |

FOREIGN PATENT DOCUMENTS

| | | |
|---|---|---|
| JP | 8255800 | 10/1996 |
| JP | 200050909171 A | 7/2000 |
| JP | 2002198320 A | 7/2002 |
| JP | 2003045818 | 2/2003 |
| WO | WO-99/50606 | 10/1999 |

OTHER PUBLICATIONS

Japanese Notice of Reasons for Rejection, Dispatch Date Mar. 4, 2008, for Japanese Patent Application No. P2004-232584.

Japanese Final Rejection, Dispatch Date Mar. 24, 2009, for Japanese Patent Application No. P2004-232584.

* cited by examiner

| G1 (%) | G2 (%) | | | | | | | | | | |
|---|---|---|---|---|---|---|---|---|---|---|---|
| | WA | WB | WC | WD | WE | WF | WG | WH | WI | WJ | WK |
| 18.0 | 25.0 | 24.5 | 24.5 | 24.0 | 23.5 | 23.5 | 23.5 | - | - | - | - |
| 20.0 | 28.0 | 27.0 | 27.0 | 26.5 | 26.5 | 26.0 | 25.5 | - | - | - | - |
| 24.0 | 33.5 | 32.5 | 32.5 | 32.2 | 31.5 | 31.0 | 30.5 | 27.0 | - | - | - |
| 26.0 | 36.5 | 35.5 | 34.5 | 34.5 | 34.0 | 34.0 | 33.5 | 29.5 | 27.5 | 27.5 | 26.5 |
| 28.0 | - | - | - | - | - | - | - | 32.5 | 30.0 | 29.5 | 28.5 |
| 30.0 | - | - | - | - | - | - | - | - | 32.5 | 31.0 | 30.0 |

(B)

| G1 (%) | G2/G1 | | | | | | | | | | |
|---|---|---|---|---|---|---|---|---|---|---|---|
| | WA | WB | WC | WD | WE | WF | WG | WH | WI | WJ | WK |
| 18.0 | 1.39 | 1.36 | 1.36 | 1.33 | 1.31 | 1.31 | 1.31 | - | - | - | - |
| 20.0 | 1.40 | 1.35 | 1.35 | 1.33 | 1.33 | 1.30 | 1.28 | - | - | - | - |
| 24.0 | 1.40 | 1.35 | 1.35 | 1.34 | 1.31 | 1.29 | 1.27 | 1.13 | - | - | - |
| 26.0 | 1.40 | 1.37 | 1.33 | 1.33 | 1.31 | 1.31 | 1.29 | 1.13 | 1.06 | 1.06 | 1.02 |
| 28.0 | - | - | - | - | - | - | - | 1.16 | 1.07 | 1.05 | 1.02 |
| 30.0 | - | - | - | - | - | - | - | - | 1.08 | 1.03 | 1.00 |
| AVERAGE | 1.40 | 1.36 | 1.35 | 1.33 | 1.31 | 1.30 | 1.28 | 1.14 | 1.07 | 1.05 | 1.01 |

| G1 (%) | G2 (%) | | | | |
|---|---|---|---|---|---|
| | W5 | W6 | W7 | W8 | W9 |
| 20.0 | 24.0 | 26.0 | 25.5 | 27.0 | 27.0 |
| 22.0 | 27.0 | 29.5 | 28.5 | 30.0 | 30.0 |
| 24.0 | 29.5 | 31.5 | 31.0 | 32.5 | 32.5 |
| 26.0 | 31.0 | 34.5 | 33.5 | 35.0 | 35.5 |

(B)

| G1 (%) | G2/G1 | | | | |
|---|---|---|---|---|---|
| | W5 | W6 | W7 | W8 | W9 |
| 20.0 | 1.20 | 1.30 | 1.28 | 1.35 | 1.35 |
| 22.0 | 1.23 | 1.34 | 1.30 | 1.36 | 1.36 |
| 24.0 | 1.23 | 1.31 | 1.29 | 1.35 | 1.35 |
| 26.0 | 1.19 | 1.33 | 1.29 | 1.35 | 1.37 |
| AVERAGE | 1.21 | 1.32 | 1.29 | 1.35 | 1.36 |

METHOD OF DETERMINING THERMAL PROPERTY OF SUBSTRATE AND METHOD OF DECIDING HEAT TREATMENT CONDITION

TECHNICAL FIELD

The present invention relates to a substrate thermal property determining method and a thermal process condition determining method.

BACKGROUND ART

Rapid thermal process (RTP) has conventionally been known as a thermal processing method used in the manufacturing of semiconductor devices and the like (see, for example, Patent Document Nos. 1 and 2). An example of rapid thermal processing apparatus used in the RTP comprises a lamp for heating a substrate, a temperature sensor (e.g., pyrometer) arranged so as to oppose the lamp, and an edge ring for holding the substrate between the lamp and the temperature sensor. When the substrate inserted between the lamp and the temperature sensor is irradiated with infrared rays by using the lamp, the temperature of the substrate rises rapidly. The temperature sensor detects the heat radiated from the substrate.

Patent Document 1: Japanese Patent Publication No. 2711239

Patent Document 2: Japanese Translated International Patent Application Laid-Open No. 2002-510153

DISCLOSURE OF THE INVENTION

Problem to be Solved by the Invention

Meanwhile, an open-loop step which raises the temperature of the substrate under open-loop control and a closed-loop step which raises the temperature of the substrate under closed-loop control can successively be carried out in the RTP.

In the open-loop step, for example, the substrate is irradiated with infrared rays for about 30 seconds by using the lamp, whereby the temperature of the substrate rises from 250° C. to 400° C. Here, for raising the temperature of the substrate uniformly and rapidly while preventing the substrate from being warped and broken caused by thermal stresses, the lamp power (electric power applied to the lamp) is kept at a fixed level which has been optimized beforehand. Such warpage and breakage become more apparent in silicon wafers having a diameter of 300 mm than in those having a diameter of 200 mm.

In the closed-loop step, on the other hand, temperature data sequentially outputted from the temperature sensor and a predetermined set temperature are compared with each other, and the lamp power is automatically adjusted while using the result of comparison.

Here, the optimal value of the lamp power in the open-loop step depends on a thermal property (e.g., infrared absorption characteristic or infrared transmission characteristic) of the substrate. However, the thermal property of the substrate is hard to determine, so that the optimal value of the lamp power is usually determined by trial and error.

Therefore, it is an object of the present invention to provide a method which can determine a thermal property of a substrate in a short time and a method which can determine a thermal process condition of an open-loop step.

Means for Solving Problem

For solving the problem mentioned above, the substrate thermal property determining method of the present invention comprises the steps of obtaining, in a rapid thermal processing apparatus comprising a lamp for heating a substrate and a temperature sensor arranged so as to oppose the lamp, temperature data sequentially outputted from the temperature sensor while subjecting the substrate disposed between the lamp and the temperature sensor to pulsed heating with the lamp; and determining a thermal property of the substrate by using the temperature data. Here, "pulsed heating" refers to heating with an energy ray whose amount of energy repeatedly changes in a pulsed fashion, for example. The same applies hereinafter.

When an energy ray emitted from the lamp is absorbed by a substrate, the substrate is heated. The temperature sensor detects the heat radiated from the heated substrate, and sequentially outputs temperature data. When a part of the energy ray is transmitted through the substrate, the temperature sensor also detects the energy ray transmitted through the substrate. Since the obtained temperature data contains information concerning the thermal property of the substrate, the substrate thermal property determining method of the present invention can determine the thermal property of the substrate in a short time. Further, the use of pulsed heating makes it possible to heat the substrate in a short time while fully suppressing the warpage, breakage, and the like thereof.

Preferably, a pulse width in the pulsed heating is at least 1 second. In this case, the substrate can be heated in a short time by the pulsed heating. Here, the "pulse width" refers to the time from the half-maximum point in the leading edge of a pulse to the half-maximum point in the trailing edge thereof, for example. The same applies hereinafter.

Preferably, the pulse width in the pulsed heating is 10 seconds or less. This can restrain the substrate from drastically raising its temperature, and thus can suppress the warpage and breakage of the substrate.

The thermal process condition determining method of the present invention is a method of determining, in a rapid thermal processing apparatus comprising a lamp for heating a substrate and a temperature sensor arranged so as to oppose the lamp, a thermal process condition of an open-loop step for raising a temperature of the substrate disposed between the lamp and the temperature sensor under open-loop control, the method comprising the steps of obtaining temperature data sequentially outputted from the temperature sensor while subjecting the substrate to pulsed heating with the lamp in the rapid thermal processing apparatus; and determining the thermal process condition of the open-loop step by using the temperature data.

When an energy ray emitted from the lamp is absorbed by a substrate, the substrate is heated. The temperature sensor detects the heat radiated from the heated substrate, and sequentially outputs temperature data. When a part of the energy ray is transmitted through the substrate, the temperature sensor also detects the energy ray transmitted through the substrate. Since the obtained temperature data contains information concerning the thermal property of the substrate, the thermal process condition determining method of the present invention can determine an optimal thermal process condition of the open-loop step which depends on the thermal property of the substrate in a short time. Further, the use of pulsed heating makes it possible to heat the substrate in a short time while fully suppressing the warpage, breakage, and the like thereof.

Preferably, a pulse width in the pulsed heating is at least 1 second. In this case, the substrate can be heated in a short time by the pulsed heating.

Preferably, the pulse width in the pulsed heating is 10 seconds or less. This can restrain the substrate from drastically raising its temperature, and thus can suppress the warpage and breakage of the substrate.

Preferably, the step of determining the thermal process condition of the open-loop step determines the thermal process condition of the open-loop step by using maximum and minimum values of the temperature data in a measurement period of the temperature data. Taking account of the maximum and minimum values can easily determine the thermal process condition of the open-loop step.

The thermal process condition of the open-loop step includes a first thermal process condition for raising a temperature of a first region including a center part of the substrate and a second thermal process condition for raising a temperature of a second region of the substrate surrounding the center part of the substrate and having a thermal property different from that of the first region, whereas the step of determining the thermal process condition of the open-loop step comprises the steps of determining the first thermal process condition by using the temperature data, calculating a ratio of the second thermal process condition to first thermal process condition by using the temperature data, and determining the second thermal process condition by using the first thermal process condition and the ratio.

This thermal process condition determining method can make the in-plane temperature difference of the substrate smaller than that in the case where the first and second regions of the substrate are heated under the same thermal process condition.

Preferably, the step of determining the first thermal process condition determines the first thermal process condition by using maximum and minimum values of the temperature data in a measurement period of the temperature data, and the step of calculating the ratio calculates the ratio by using the maximum and minimum values of the temperature data in the measurement period of the temperature data. Taking account of the maximum and minimum values can easily determine the first thermal process condition.

Effect of the Invention

The present invention can provide a method which can determine a thermal property of a substrate in a short time and a method which can determine a thermal process condition of an open-loop step.

BRIEF DESCRIPTION OF THE DRAWINGS

FIG. 10 A chart showing relationships between center lamp power G1 (%) and peripheral lamp power G2 (%).

FIG. 15 A chart showing relationships between center lamp power G1 (%) and peripheral lamp power G2 (%).

FIG. 16(A) is a graph showing the relationship between the time required for raising the temperature data obtained from the temperature sensor from 250° C. to 380° C. and the ratio G2/G1 when wafers are subjected to continuous heating, whereas FIG. 16(B) is a graph showing the relationship between the cycle of pulses required for the temperature data obtained from the temperature sensor to reach a predetermined temperature and the relationship between the ratio G2/G1 when the wafers are subjected to pulsed heating.

EXPLANATIONS OF NUMERALS AND LETTERS

9 . . . lamp; T1 to T7 . . . temperature sensor; 1 . . . rapid thermal processing apparatus; W . . . wafer (substrate); L1 . . . open-loop step; T1max . . . maximum value of temperature data; T1min . . . minimum value of temperature data; $b_1$ . . . center part of the substrate (first region of the substrate); $b_2$ . . . peripheral edge of the substrate (second region of the substrate).

BEST MODES FOR CARRYING OUT THE INVENTION

In the following, preferred embodiments of the present invention will be explained with reference to the drawings. In the explanation of the drawings, elements identical or equivalent to each other will be referred to with numerals or letters identical to each other without repeating their overlapping descriptions.

First Embodiment

Rapid Thermal Processing Apparatus

Figure 1:
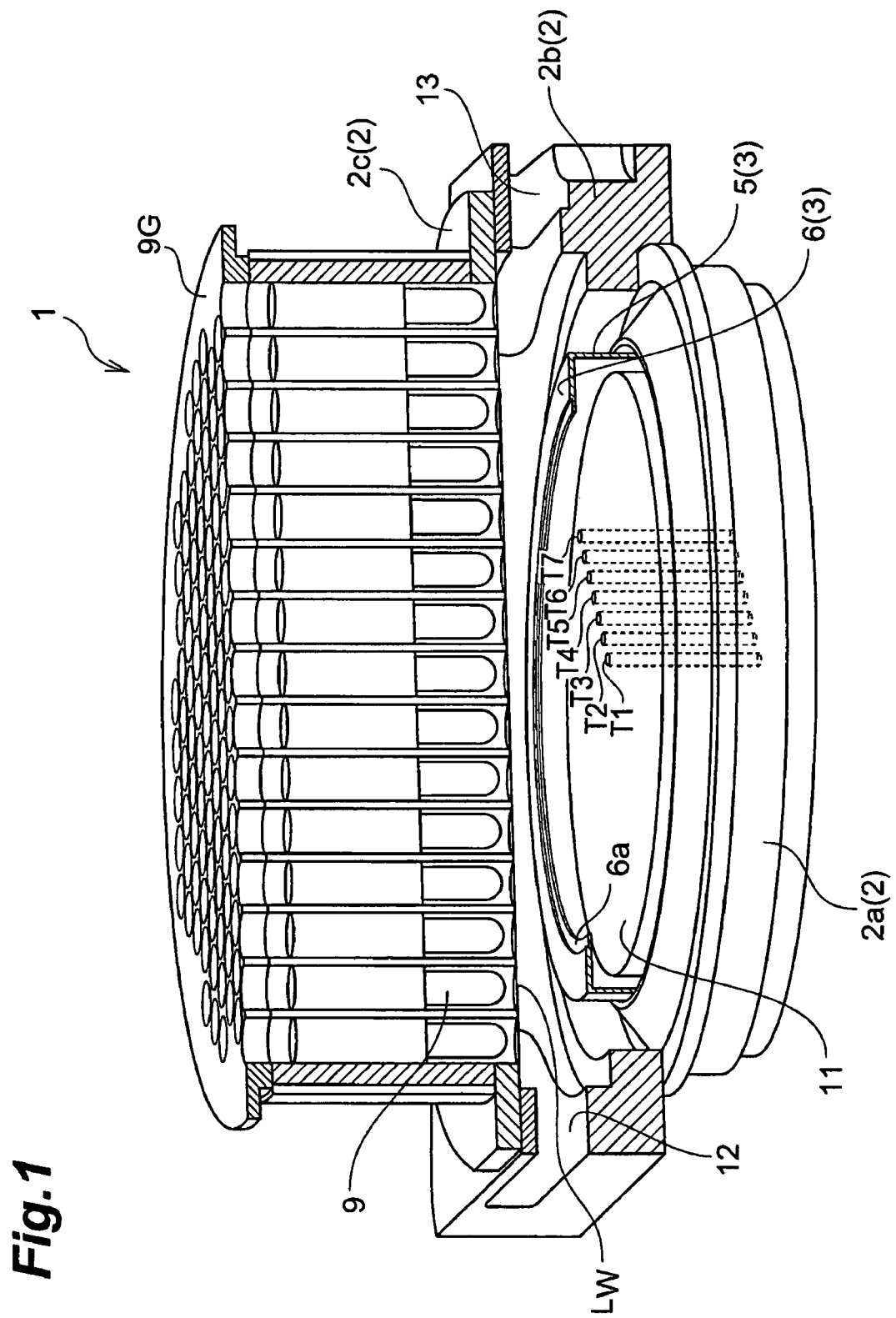
FIG. 1 A perspective view showing an example of rapid thermal processing apparatus (RTP apparatus).
Figure 2:
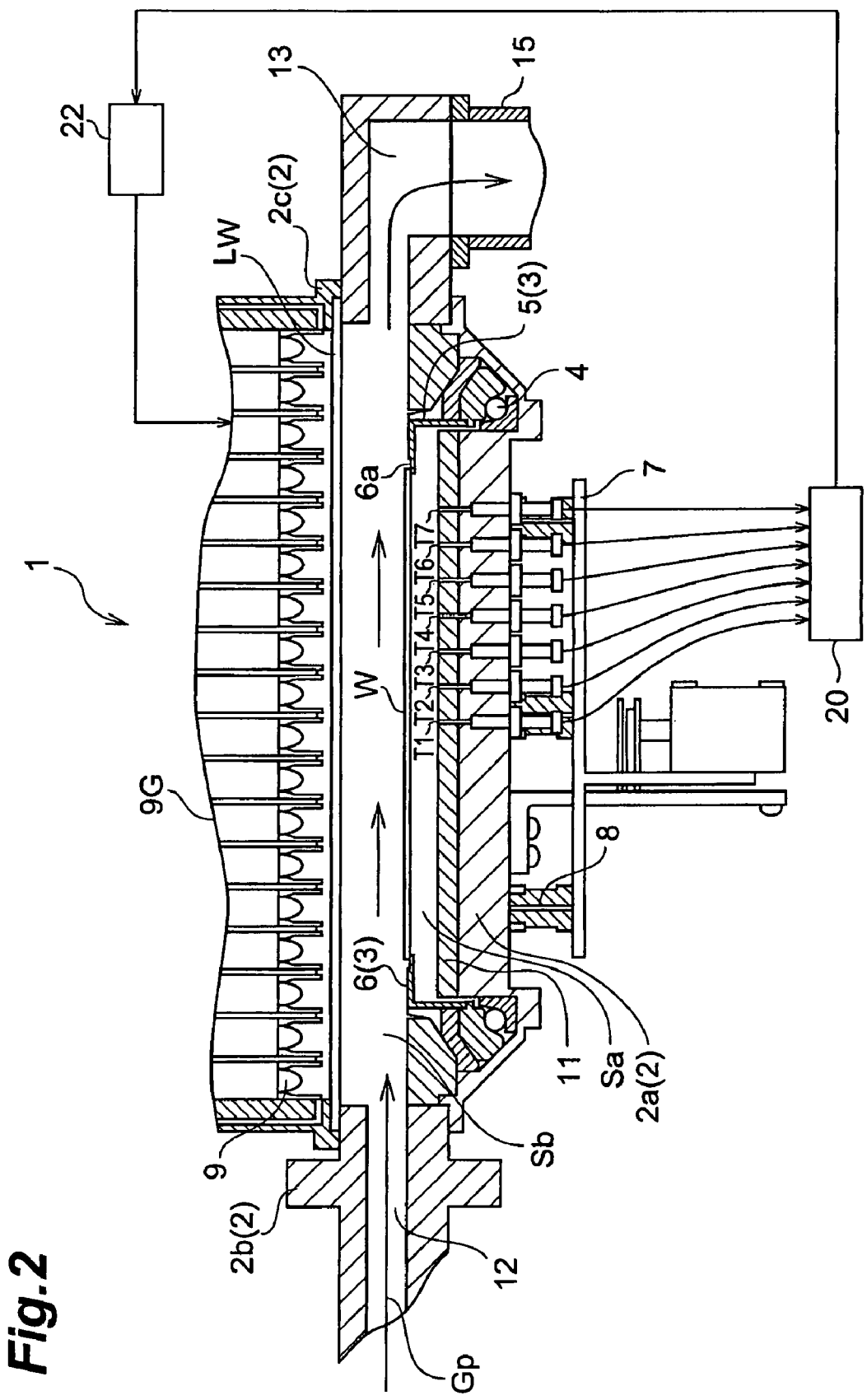
FIG. 2 A partly enlarged sectional view of the rapid thermal processing apparatus of FIG. 1.

First, a rapid thermal processing apparatus (RTP apparatus) will be explained with reference to FIGS. 1 to 5. FIG. 1 is a perspective view (partly sectional view) showing an example of rapid thermal processing apparatus, whereas FIG. 2 is a partly enlarged sectional view of the rapid thermal processing apparatus of FIG. 1. The rapid thermal processing apparatus 1 is a single-wafer rapid thermal processing apparatus for thermally processing a wafer W (substrate) such as silicon wafer while controlling the temperature thereof, for example. The rapid thermal processing apparatus 1 is used for manufacturing a semiconductor device such as LSI, for example. The rapid thermal processing apparatus 1 is equipped with a chamber 2 constituted by a base part 2a, a side wall part 2b, and a lid part 2c.

A substrate supporting part 3 such as susceptor for supporting the wafer W is installed within the chamber 2. The substrate supporting part 3 is constructed by a cylindrical frame 5 rotatably attached to the base part 2a with a bearing 4 or a magnetic levitation type rotating mechanism and an edge ring 6 disposed at an upper end of the cylindrical frame 5. The inner edge part of the edge ring 6 is provided with a supporting step 6a for supporting the edge part of the wafer W.

Here, a closed space Sa defined by the base part 2a, substrate supporting part 3, and wafer W is formed on the back side of the wafer W in the state where the wafer W is supported by the substrate supporting part 3 (see FIG. 2). When the edge part of the wafer W is mounted on the supporting step 6a of the edge ring 6, a slight gap may occur between the wafer W and edge ring 6 because of the structure of the apparatus.

A lift mechanism 7 for allowing the substrate supporting part 3 to support the wafer W transported into the chamber 2 by a transportation robot (not shown) is provided under the base part 2a. This lift mechanism 7 has a plurality of (e.g., three) support pins 8 which pass through the base part 2a and lift the wafer W.

In the side wall part 2b of the chamber 2, a gas supply port 12 and a gas discharge port 13 are provided on the sides opposite to each other. A gas supply system (not depicted) for supplying an $N_2$ gas Gp as a process gas to the outside of the closed space Sa within the chamber 2, i.e., a space Sb on the front side of the wafer W, is connected to the gas supply port 12. Examples of the process gas include $O_2$, $NH_3$, NO, $N_2O$, and $H_2$ gases in addition to the $N_2$ gas. On the other hand, a gas discharge system (not shown) for discharging the gas within the space Sb to the outside of the chamber 2 is connected to the gas discharge port 13.

A lamp group 9G constituted by a plurality of lamps 9 for heating the wafer W supported by the substrate supporting part 3 is arranged on the upper side of the lid part 2c of the chamber 2. For example, halogen lamps are preferably used as the lamps 9. The lid part 2c is provided with a circular lamp window Lw, and an energy ray (light) such as infrared ray emitted from the lamps 9 is transmitted through the lamp window Lw and reaches the wafer W. The wafer W raises its temperature when it absorbs the energy ray. The base part 2a is provided with temperature sensors T1 to T7 such as pyrometers for optically detecting the radiant heat from the wafer W or the energy ray transmitted through the wafer W. Therefore, the lamp group 9G and the temperature sensors T1 to T7 are arranged such as to oppose each other in the rapid thermal processing apparatus 1, while the wafer W is arranged between the lamp group 9G and the temperature sensors T1 to T7.

In a circular plate 11 surrounded by the substrate supporting part 3 in the base part 2a, the temperature sensors T1 to T7 are built within a substantially fan-shaped sensor installation area including the center of the plate and a part of its periphery edge while having a predetermined angle (e.g., 90 degrees). For example, the temperature sensors T1 to T7 are aligned successively from the center to periphery edge of the circular plate 11. The above-mentioned closed space Sa is an optically completely closed space, whereby the detection by the optical temperature sensors T1 to T7 can be achieved without any problem utilizing the closed space Sa.

As shown in FIG. 2, a temperature controller 20 for collecting respective temperature data sequentially outputted from the temperature sensors T1 to T7 is optically connected to the temperature sensors T1 to T7. A lamp driver 22 for driving the lamp group 9G is connected to the temperature controller 20. The temperature data obtained from the temperature sensors T1 to T7 are used as an index of the temperature of the wafer W. Using the temperature data, the temperature controller 20 determines an optimal value of the electric power applied to the lamps 9 (hereinafter referred to as lamp power). Thereafter, the temperature controller 20 outputs a signal to the lamp driver 22. As a result, the lamps 9 emit an energy ray having a desirable amount of energy from the lamps 9 toward the wafer W. Thus performing closed-loop control adjusts the temperature of the wafer W to a desirable set value.

Figure 3:
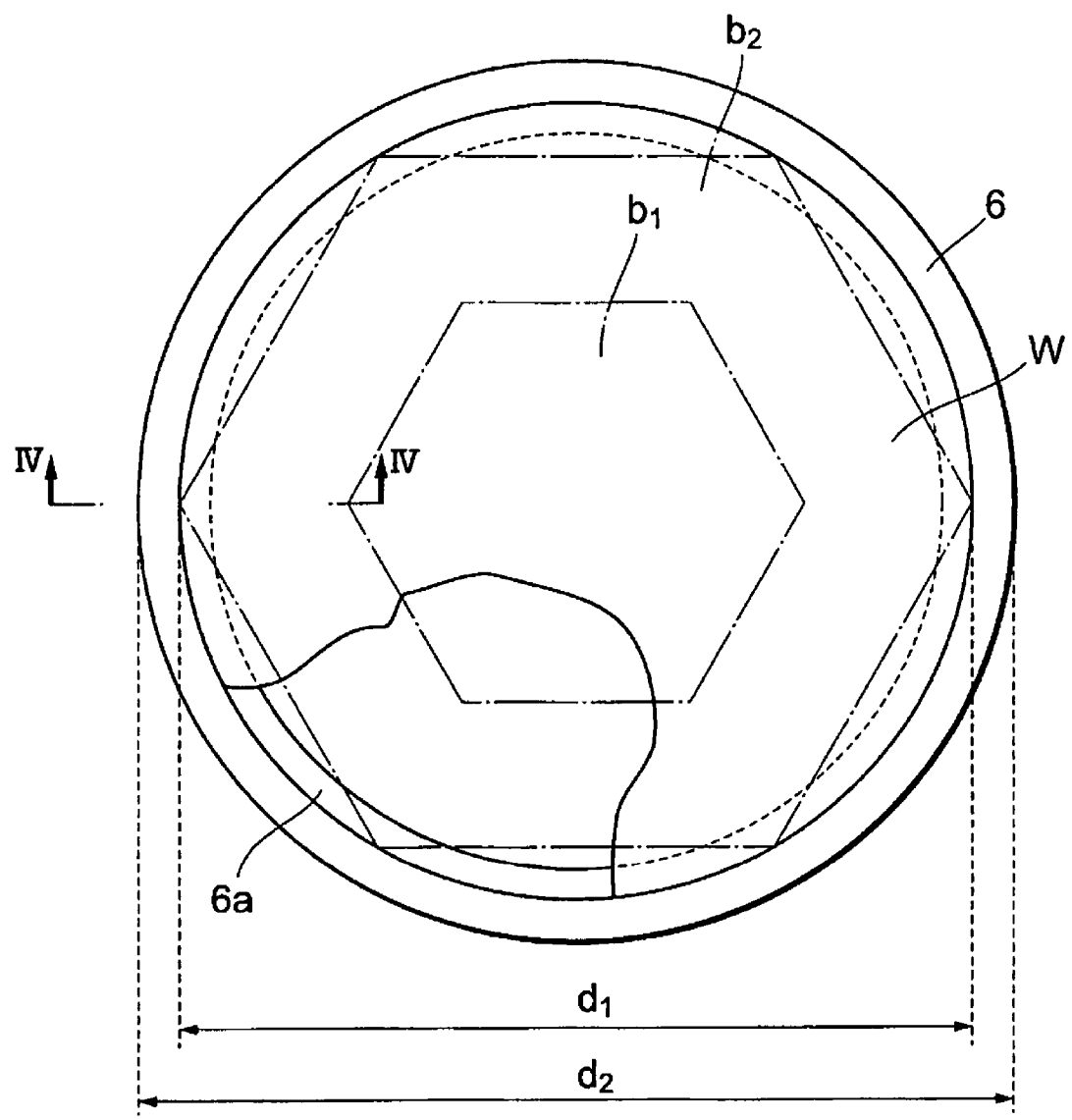
FIG. 3 A plan view of a wafer seen from the position of a lamp group.
Figure 4:
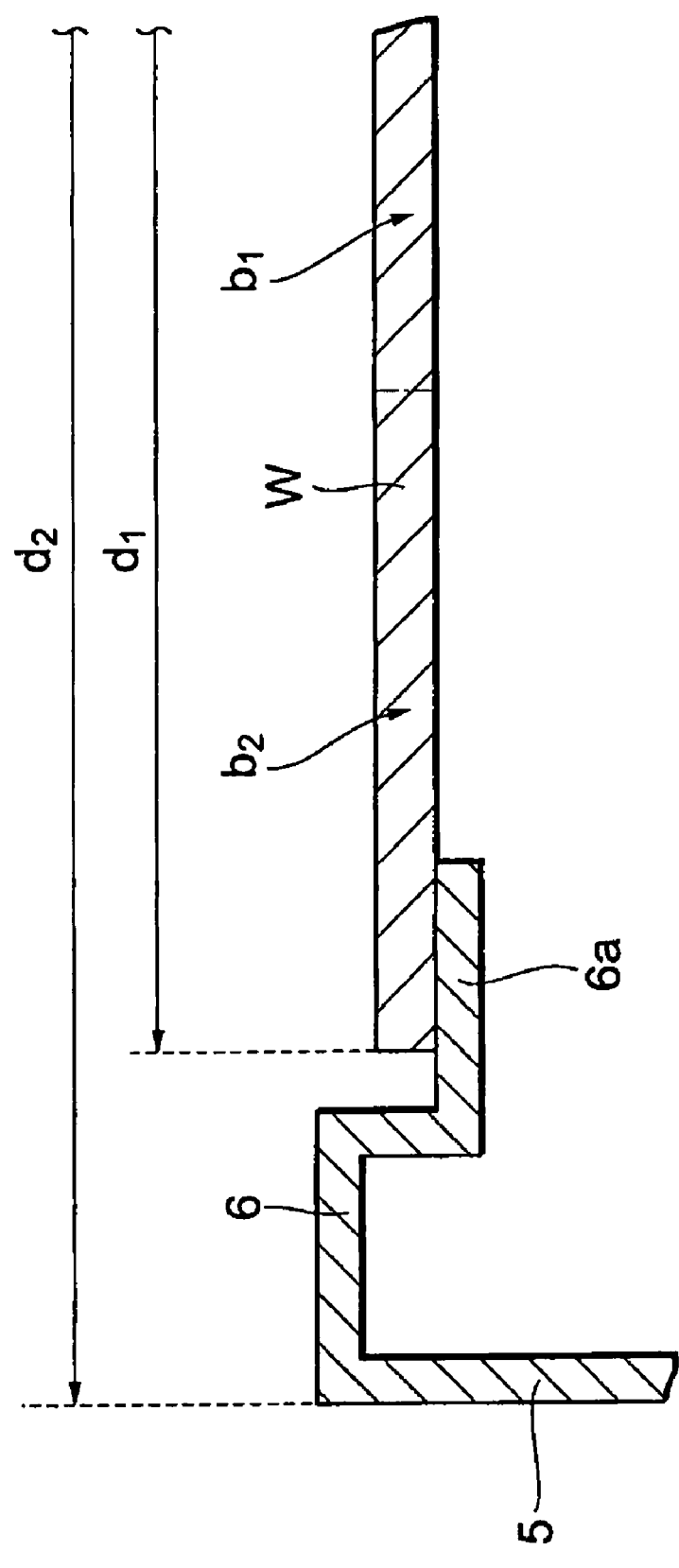
FIG. 4 A sectional view taken along the line IV-IV shown in FIG. 3.

FIG. 3 is a plan view of the wafer W seen from the position of the lamp group 9G, whereas FIG. 4 is a sectional view taken along the line IV-IV shown in FIG. 3. For convenience, FIG. 3 omits a part of the wafer W in order to illustrate a part of the supporting step 6a of the edge ring 6. The outer diameter $d_2$ of the edge ring 6 is greater than the diameter $d_1$ of the wafer W. The wafer W is supported by the supporting step 6a. The wafer W has a center part $b_1$ (first region) and a peripheral edge $b_2$ (second region) surrounding the center part $b_1$. Since the peripheral edge $b_2$ of the wafer W is in contact with the supporting step 6a of the edge ring 6, the thermal property of the peripheral edge $b_2$ depends on that of the edge ring 6 in addition to that of the wafer W. Therefore, the center part $b_1$ and the peripheral edge $b_2$ differ from each other in terms of the thermal property.

Figure 5:
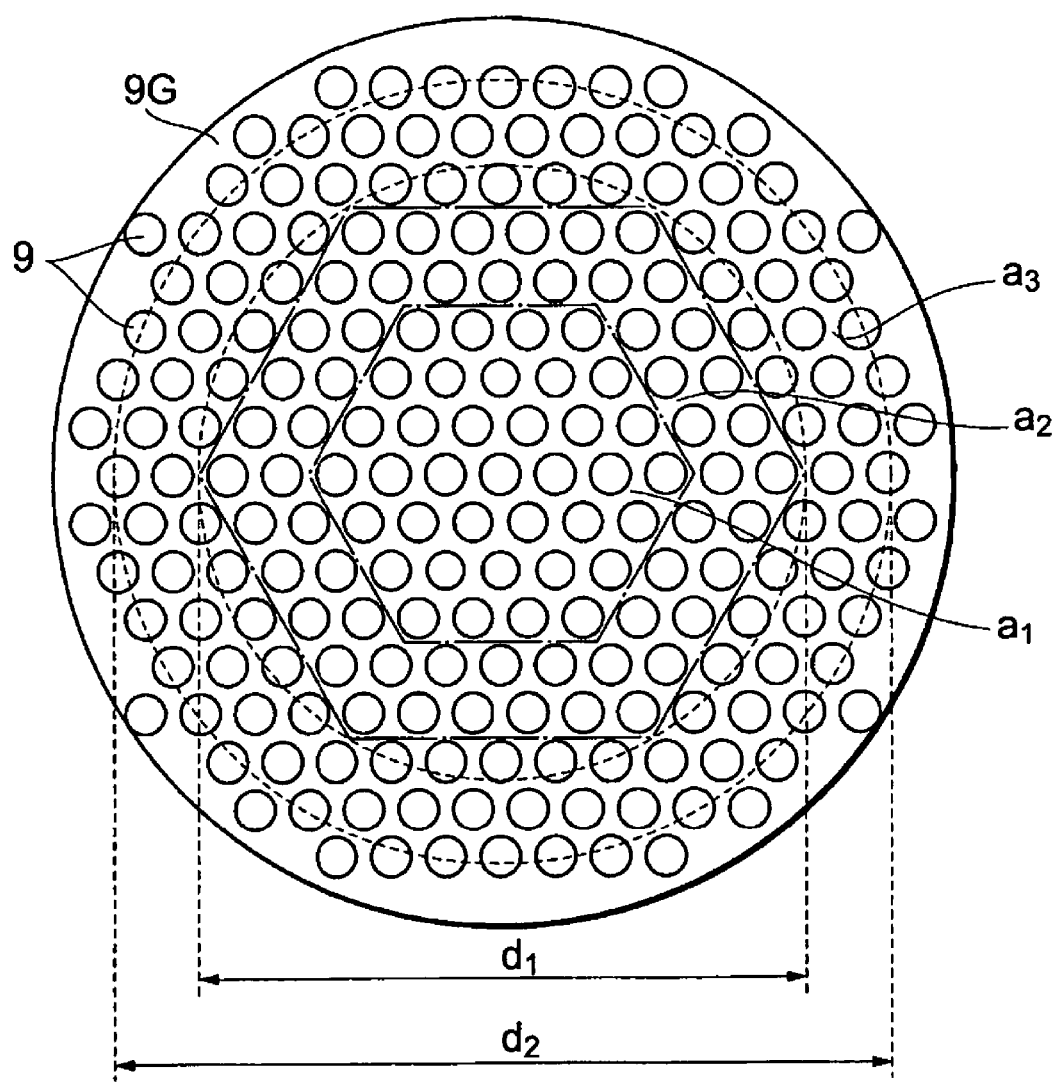
FIG. 5 A plan view of the lamp group seen from the position of the wafer.

FIG. 5 is a plan view of the lamp group 9G seen from the position of the wafer W. The lamps 9 constituting the lamp group 9G are arranged into a honeycomb form. The lamps 9 within a center region $a_1$ of the lamp group 9G are arranged so as to oppose the center part $b_1$ of the wafer W (see FIG. 3), thereby heating the center part $b_1$. The lamps 9 within a region $a_2$ surrounding the center region $a_1$ of the lamp group 9G are arranged so as to oppose the peripheral edge $b_2$ of the wafer W (see FIG. 3), thereby heating the peripheral edge $b_2$. A peripheral edge region $a_3$ is provided around the region $a_2$.

Figure 6:
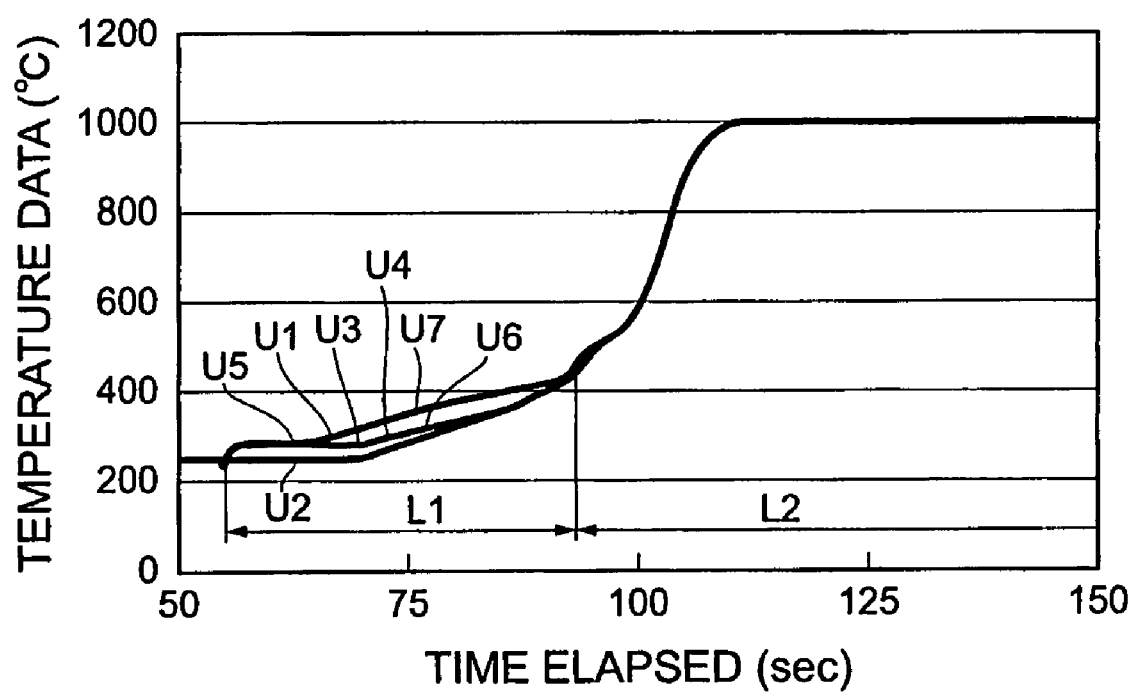
FIG. 6 A graph showing an example of temperature data sequentially outputted from temperature sensors when a wafer is subjected to a rapid thermal process by using the rapid thermal processing apparatus.

A rapid thermal process carried out by the rapid thermal processing apparatus 1 will now be explained with reference to FIG. 6. FIG. 6 is a graph showing an example of temperature data sequentially outputted from temperature sensors T1 to T7 when the wafer W is subjected to a rapid thermal process in the above-mentioned rapid thermal processing apparatus 1. In FIG. 6, the ordinate of the graph indicates temperature data (° C.) outputted from the temperature sensors T1 to T7, whereas the abscissa of the graph indicates the time elapsed (sec). In the graph, waveforms U1 to U7 represent respective temperature data sequentially outputted from the temperature sensors T1 to T7.

As shown in FIG. 6, an open-loop step L1 performing open-loop control and a closed-loop step L2 performing closed-loop step are carried out in a rapid thermal process carried out in the rapid thermal processing apparatus 1. For example, a wafer (bare silicon wafer in particular) containing silicon (Si) as its base material is likely to transmit an energy ray therethrough when its temperature is less than 400° C. Therefore, the temperature sensors T1 to T7 also detect the energy ray transmitted through the wafer W when the temperature of the wafer W is less than 400° C. Thus, the temperature data sequentially outputted from the temperature sensors T1 to T7 do not always reflect the temperature of the wafer W. Hence, the wafer W is initially heated to a temperature of about 400° C. in the open-loop step L1. Thereafter, the wafer W is heated to a temperature of about 1000° C. in the closed-loop step L2. In the example shown in FIG. 6, the rapid thermal processing conditions are a pressure of 760×133.322 Pa (760 Torr), an $O_2$ gas flow rate of 20 slm, and a heating time of 60 seconds. Here, "slm" refers to the flow rate (liter) per minute at 0° C., 1 atm. The same applies in the following explanations. With reference to the graph of FIG. 6, differences are seen among the waveforms U1 to U7 in the open-loop step L1, but hardly in the closed-loop step L2.

In the open-loop step L1 in this embodiment, the lamp powers of the lamps 9 within the center region $a_1$ and region $a_2$ shown in FIG. 5 are referred to as center lamp power G1 and peripheral edge lamp power G2, respectively. Changing the lamp power between the lamps 9 within the center region $a_1$ and the lamps 9 within the region $a_2$ can reduce the in-plane temperature difference ΔT of the wafer W when switching from the open-loop step L1 to the closed-loop step L2 (hereinafter simply referred to as in-plane temperature difference ΔT). The in-plane temperature difference ΔT is represented by the difference between the respective temperature data obtained from the temperature sensors T1 and T7, for example. Optimizing the relationship between the center lamp power G1 and peripheral edge lamp power G2 according to the species of wafer can further reduce the in-plane temperature difference ΔT. In the example shown in FIG. 6, the center lamp power G1 and peripheral lamp power G2 in the open-loop step L1 are 24% and 33% of the full power, respectively.

The lamps 9 within the peripheral region $a_3$ of the lamp group 9G shown in FIG. 5 hardly contribute to raising the temperature of the wafer W when the temperature data obtained from the temperature sensors T1 to T7 are 500° C. or less. When the lamp power of each lamp 9 within the peripheral region $a_3$ is referred to as lamp power G3, the lamp power G3 in the open-loop step L1 is fixed to 5% of the full power in the example shown in FIG. 6.

Substrate Thermal Property Determining Method and Thermal Process Condition Determining Method The substrate thermal property determining method and thermal process condition determining method in accordance with the first embodiment will now be explained. The substrate thermal property determining method in accordance with this embodiment is preferably carried out by using the rapid thermal processing apparatus 1. The thermal process condition determining method in accordance with this embodiment is favorably carried out by using the rapid thermal processing apparatus 1 prior to the rapid thermal process including the above-mentioned open-loop step L1 and closed-loop step L2.

First, the wafer W is arranged between the lamp group 9G and the temperature sensors T1 to T7 in the rapid thermal processing apparatus 1. Subsequently, temperature data sequentially outputted from the temperature sensors T1 to T7 are obtained while the wafer W is subjected to pulsed heating with the lamps 9 of the lamp group 9G. When the wafer W is subjected to pulsed heating, the energy ray emitted from the lamps 9 is absorbed by the wafer W. The temperature sensors T1 to T7 detect the heat radiated from the heated wafer W, and sequentially output temperature data to the temperature controller 20. When a part of the energy ray is transmitted through the wafer W, the temperature sensors T1 to T7 also detect the energy ray transmitted through the wafer W.

Figure 7:
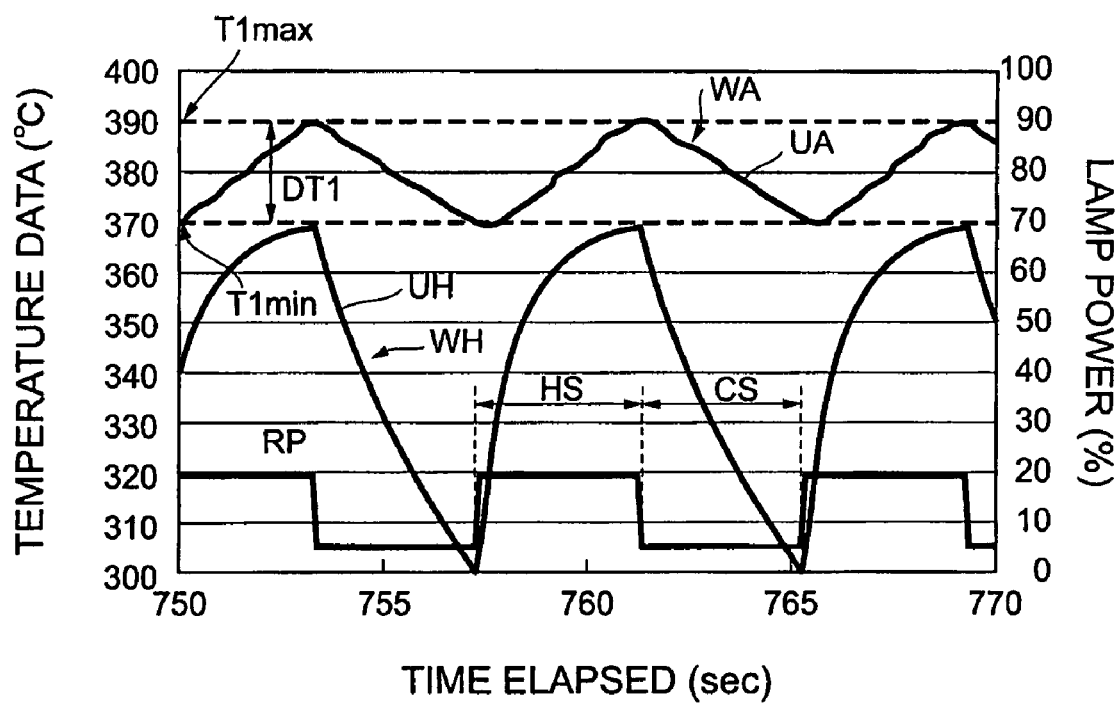
FIG. 7 A graph showing an example of temperature data sequentially outputted from a temperature sensor when wafers having thermal properties different from each other are subjected to pulsed heating.

FIG. 7 is a graph showing an example of temperature data sequentially outputted from the temperature sensor T1 when wafers WA, WH having thermal properties different from each other are subjected to pulsed heating. The wafers WA, WH are specific examples of the above-mentioned wafer W.

In FIG. 7, one ordinate of the graph indicates the temperature data (° C.) sequentially outputted from the temperature sensor T1, whereas the other ordinate represents the lamp power (%) in the case where the full power of the lamps 9 is 100%. The abscissa of the graph shows the time elapsed (sec).

Waveforms UA, UH in the graph represent temperature data obtained in the respective cases using the wafers WA, WH. Waveform RP in the graph indicates the change in lamp power with time, and illustrates a waveform in which a plurality of pulses are repeated. In the waveform RP, a plurality of heating period HS and a plurality of cooling period CS are alternately performed, while one pulse is positioned in one heating span HS. The cooling period CS fully prevent the wafers WA, WH from warping, breaking, and so forth.

In the example shown in FIG. 7, each of the heating period HS and cooling period CS lasts 4 seconds. The times of the heating period HS and cooling period CS may be the same or different from each other. In the heating period HS, the lamps 9 within the center region $a_1$ and region $a_2$ of the lamp group 9G each have a lamp power which is 19% of the full power, for example, whereas the lamps 9 within the peripheral edge region $a_3$ each have a lamp power which is 5% of the full power, for example. In the cooling period CS, the lamps 9 within the center region $a_1$, region $a_2$, and peripheral edge region $a_3$ each have a lamp power which is 5% of the full power, for example. The other conditions at the time of heating are a pressure of 740×133.322 Pa (740 Torr) and an $N_2$ gas flow rate of 10 slm.

The temperature data represented by the above-mentioned waveforms UA, UH include respective information items concerning the thermal properties of the wafers WA, WH. Therefore, using the temperature data represented by the waveforms UA, UH can easily determine the thermal properties of the wafers WA, WH easily in a short time as follows, for example. Also, the warpage, breakage, and the like of the wafers WA, WH can fully be suppressed in the case of pulsed heating. Here, FIG. 7 shows a part (time elapsed: 750 to 770 seconds) of the measurement period of the temperature data represented by the waveforms UA, UH. In the measurement period, the local maxima and minima of the temperature data are saturated as shown in FIG. 7. For example, the "measurement period" refers to a period in which the difference between adjacent local minima of temperature data is within ±0.2° C.

In the example shown in FIG. 7, the maximum value T1max and minimum value T1min in the measurement period of the temperature data represented by the waveforms UA, UH are about 390° C. and about 370° C., respectively. In this case, the difference ΔT1 (ΔT1=T1max−T1min) between the maximum value T1max and minimum value T1min is about 20° C. When the maximum value T1max and minimum value T1min are large, it indicates that the wafer is easily warmed by absorbing the energy ray. When the difference ΔT1 is large, it indicates that the wafer easily transmits the energy ray therethrough.

In the example shown in FIG. 7, the temperature data of the waveform UA ascends linearly in the heating period HS and descends linearly in the cooling period CS. On the other hand, the temperature data of the waveform UH ascends in an upwardly convex fashion in the heating period HS and descends in a downwardly convex fashion in the cooling period CS. These indicate that the wafer WH is easier to transmit the energy ray therethrough than the wafer WA.

Using temperature data obtained by subjecting a wafer having an unknown thermal property to the above-mentioned pulsed heating, the thermal property of the wafer can easily be determined in a short time in the same manner. Also, the pulsed heating can fully suppress the warpage, breakage, and the like of the wafer.

Subsequently, using the temperature data sequentially outputted from the temperature sensors T1 to T7 when subjecting the wafer W to pulsed heating with the lamps 9 of the lamp group 9G, the lamp power (thermal process condition) of the lamps 9 in the open-loop step L1 shown in FIG. 6 is determined. Examples of the lamp power include the above-mentioned center lamp power G1 (first thermal process condition G1) and peripheral edge lamp power G2 (second thermal process condition G2). Using the temperature data obtained by the above-mentioned pulsed heating in this case can determine the center lamp power G1 and peripheral edge lamp power G2 in the open-loop step L1 easily in a short time as will be explained later. Also, the pulsed heating can fully suppress the warpage, breakage, and the like of the wafer W.

When the wafer WA, WH are used as the wafer W, for example, temperature data represented by the waveforms UA, UH are obtained by pulsed heating as shown in FIG. 7. Using the maximum value Tmax and minimum value Tmin of the temperature data in the measurement period of the temperature data can easily determine the center lamp power G1 and peripheral edge lamp power G2. This will be explained in detail in the following.

Determination of Center Lamp Power G1

First, using the maximum value T1max and the difference ΔT1 between the maximum value T1max and minimum value T1min in the temperature data represented by the above-mentioned waveforms UA, UH, the absorption correction coefficient Kab represented by the following expression (1) is defined:

$$Kab = 1 - (\Delta T1/T1\max) \quad (1)$$

Multiplying the absorption correction coefficient Kab by the minimum value T1min yields (Kab)·(T1min). Using this (Kab)·(T1min) and the linear function represented by the following expression (2), the center lamp power G1 is determined:

$$G1 = p \times (Kab) \cdot (T1\min) + q \quad (2)$$

In the expression, p and q are predetermined constants.

Figure 8:
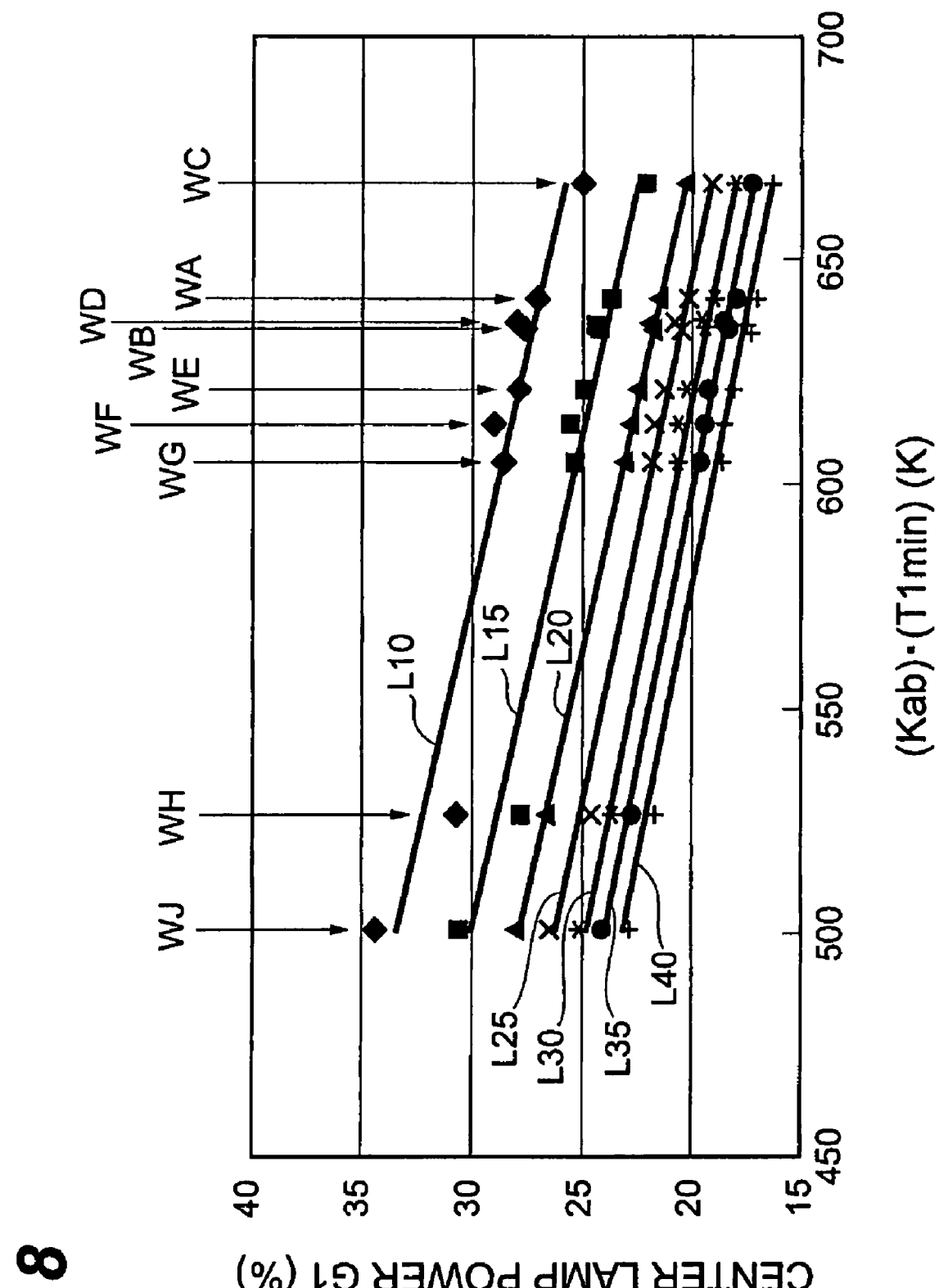
FIG. 8 A graph showing relationships between (Kab)·(T1min) and center lamp power G1.

FIG. 8 is a graph showing relationships between (Kab)·(T1min) and the center lamp power G1. In FIG. 8, the ordinate and abscissa of the graph indicate the center lamp power G1 (%) and (Kab)·(T1min) (K), respectively. Approximate lines L10, L15, L20, L25, L30, L35, and L40 in the graph are specific examples of the linear function represented by the above-mentioned expression (2). The approximate lines L10, L15, L20, L25, L30, L35, and L40 correspond to the respective cases where the time required for the temperature data outputted from the temperature sensor T1 to rise from 250° C. to 400° C. (hereinafter referred to as time rise time) is 10, 15, 20, 25, 30, 35, and 40 seconds.

The approximate lines L10, L15, L20, L25, L30, L35, and L40 are obtained as follows. First, the absorption correction coefficient Kab and minimum value T1min are calculated from the temperature data sequentially outputted from the temperature sensor T1 when wafers WA to WH, WJ having thermal properties different from each other are subjected to pulsed heating. On the other hand, the center lamp powers G1 where the temperature rise time becomes 10, 15, 20, 25, 30, 35, and 40 seconds are experimentally determined for each of the wafers WA to WH, WJ. Then, the center lamp power G1 is plotted against (Kab)·(T1min), whereby the graph of FIG. 8 is obtained.

For wafers having unknown thermal properties, (Kab)·(T1min) can similarly be calculated from the temperature data obtained by pulsed heating. Further, setting a desirable temperature rise time and using the approximate line L10, L15, L20, L25, L30, L35, or L40 corresponding to this temperature rise time can easily determine the center lamp power G1 in a short time. In the case where the temperature rise time is 30 seconds, for example, the center lamp power G1 is determined by using the (Kab)·(T1min) calculated from the temperature data obtained when subjecting the wafer to pulsed heating and the approximate line L30.

Figure 9:
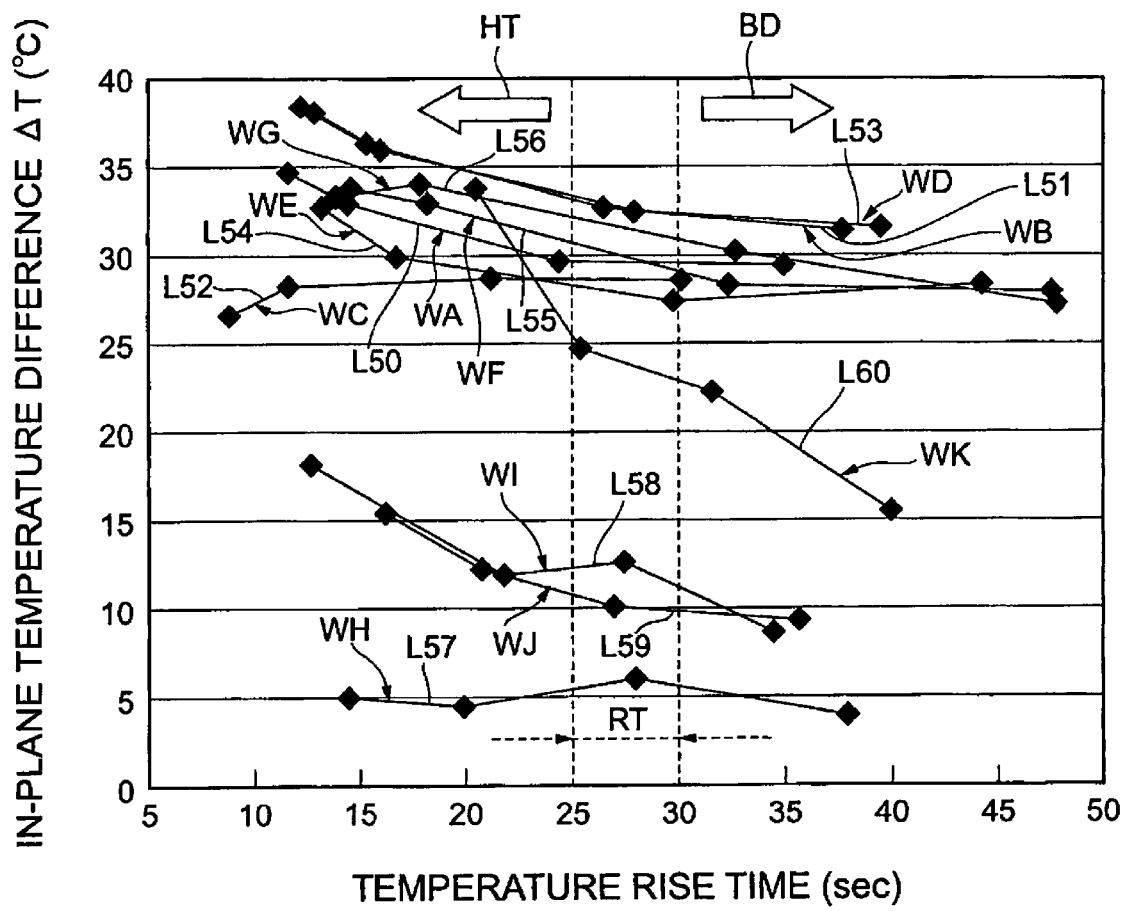
FIG. 9 A graph showing relationships between temperature rise time and in-plane temperature difference ΔT.

FIG. 9 is a graph showing relationships between the temperature rise time and in-plane temperature difference ΔT (° C.). In FIG. 9, the ordinate and abscissa of the graph indicate the in-plane temperature difference ΔT (° C.) and temperature rise time (sec), respectively. Solid lines L50 to L60 in the graph indicate the respective temperature rise times and in-plane temperature differences ΔT in the cases where wafers WA to WK having thermal properties different from each other are subjected to the rapid thermal process. The graph shows that the optimal value of temperature rise time is about 25 seconds to about 30 seconds (within region RT). When the temperature rise time exceeds 30 seconds (region BD), the open-loop step time becomes longer, whereby the rapid thermal process tends to lower its throughput. When the temperature rise time is less than 25 seconds (region HT), on the other hand, the wafers WA to WK are heated rapidly, so that the in-plane temperature difference ΔT tends to become greater. Therefore, it will be preferred if one of the approximate lines L25, L30 is used in FIG. 8, so as to determine the optimal center lamp power G1.

Calculation of Ratio G2/G1

Separately from the determination of the center lamp power G1, the ratio G2/G1 that minimizes the in-plane temperature difference ΔT is calculated. First, the ratio G2/G1 will be explained with reference to FIGS. 10(A) and 10(B).

FIGS. 10(A) and 10(B) are charts showing relationships between the center lamp power G1 (%) and peripheral lamp power G2 (%) in the open-loop step. In the examples shown in FIGS. 10(A) and 10(B), the thermal process conditions in the open-loop step are a pressure of 740×133.322 Pa (740 Torr) and an $N_2$ gas flow rate of 10 slm, for instance.

FIG. 10(A) shows results of experimentally determining the peripheral lamp power G2 minimizing the in-plane temperature difference ΔT for each center lamp power G1 while changing the center lamp power G1 within the range of 18 to 30% of the full power for the wafers WA to WK having thermal properties different from each other.

FIG. 10(B) shows the ratio G2/G1 obtained from the experimental results of FIG. 10(A). As shown in FIG. 10(B), the ratio G2/G1 is substantially a constant value even when the center lamp power G1 changes, which verifies that the ratio G2/G1 is a characteristic value of each wafer. As a value of the ratio G2/G1, an average value can be used, for example. Using the ratio G2/G1 can classify wafers according to their thermal properties. Specifically, wafers having a greater ratio of G2/G1 are found easier to warm, for example. By contrast, wafers having a smaller ratio of G2/G1 are found harder to warm.

Figure 11:
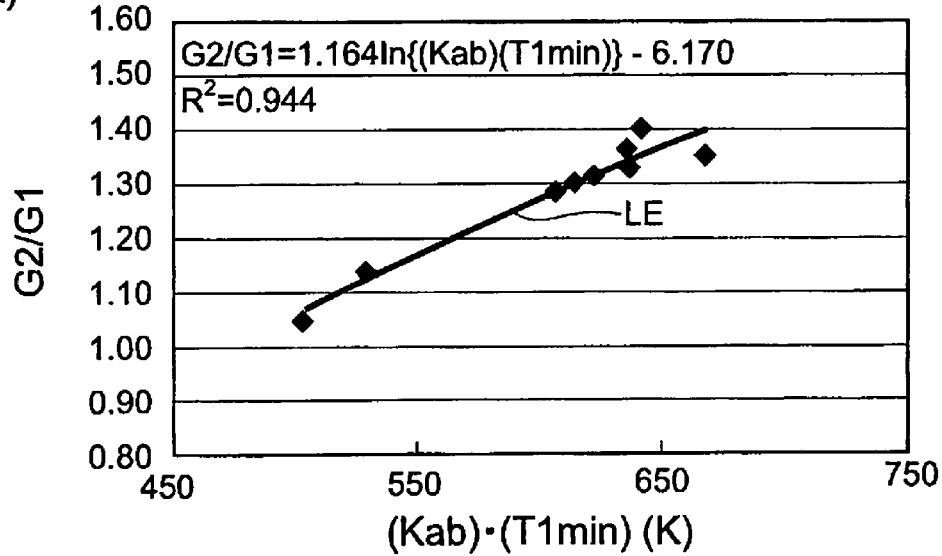
FIG. 11 A graph showing relationships between (Kab)·(T1min) and ratio G2/G1.
Figure 11:
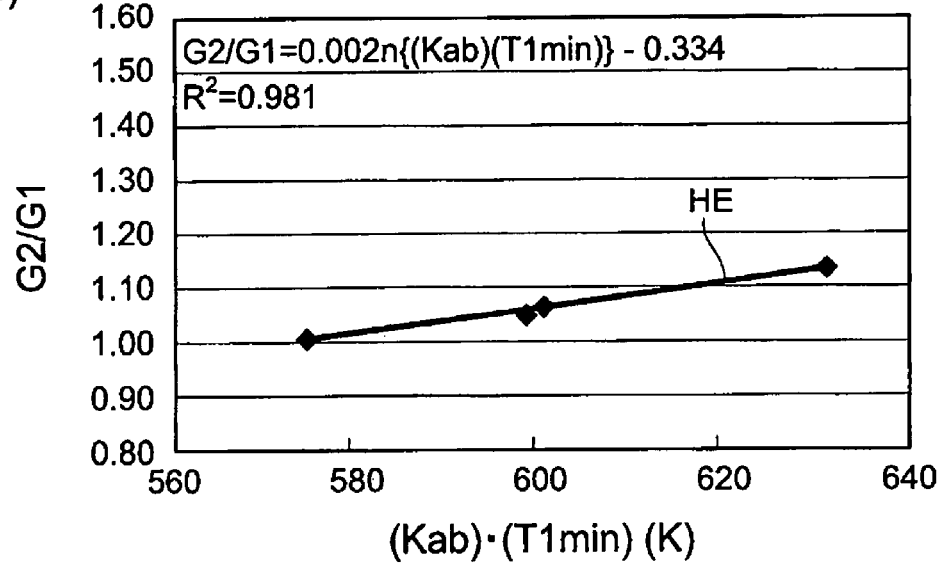

A method of calculating the ratio G2/G1 will now be explained with reference to the graphs of FIGS. 11(A) and 11(B). Each of FIGS. 11(A) and 11(B) shows the relationship between (Kab)·(T1min) and ratio G2/G1. In FIGS. 11(A) and 11(B), the ordinate and abscissa in each graph indicate the ratio G2/G1 and (Kab)·(T1min) (K), respectively.

In FIG. 11(A), solid line LE indicates results of pulsed heating obtained when the lamp power of the lamps 9 is 19%

(low power) of the full power. In one example, the lamp power of each of the lamps 9 within the center region $a_1$ and region $a_2$ of the lamp group 9G shown in FIG. 5 is 19% of the full power, for instance, whereas the lamp power of each of the lamps 9 within the peripheral region $a_3$ is 5% of the full power, for instance. The other conditions at the time of pulsed heating are a pressure of 740×133.322 Pa (740 Torr) and an $N_2$ gas flow rate of 10 slm, for example. Pulsed heating at the low power yields the temperature data represented by the waveforms UA, UH of FIG. 7, for example. When the (Kab)·(T1min) calculated by using this temperature data is put into the function represented by the solid line LE in FIG. 11(A), the ratio G2/G1 is calculated.

In FIG. 11(B), solid line HE indicates results of pulsed heating obtained when the lamp power of the lamps 9 is 23% (high power) of the full power. In one example, the lamp power of each of the lamps 9 within the center region $a_1$ and region $a_2$ of the lamp group 9G shown in FIG. 5 is 23% of the full power, for instance, whereas the lamp power of each of the lamps 9 within the peripheral region $a_3$ is 5% of the full power, for instance. The other conditions at the time of pulsed heating are a pressure of 740×133.322 Pa (740 Torr) and an $N_2$ gas flow rate of 10 slm, for example. Pulsed heating at the high power yields the temperature data sequentially outputted from the temperature sensors T1 to T7. When the (Kab)·(T1min) calculated by using this temperature data is put into the function represented by the solid line HE in FIG. 11(B), the ratio G2/G1 is calculated.

For wafers having unknown thermal properties, (Kab)·(T1min) can similarly be calculated from the temperature data obtained by pulsed heating with the low or high power. When this (Kab)·(T1min) is put into the function represented by the solid line LE in FIG. 11(A) or solid line HE in FIG. 11(B), the ratio G2/G1 can be calculated.

Determination of Peripheral Lamp Power G2

Using the center lamp power G1 and ratio G2/G1 obtained as mentioned above, the peripheral lamp power G2 is determined.

Figure 12:
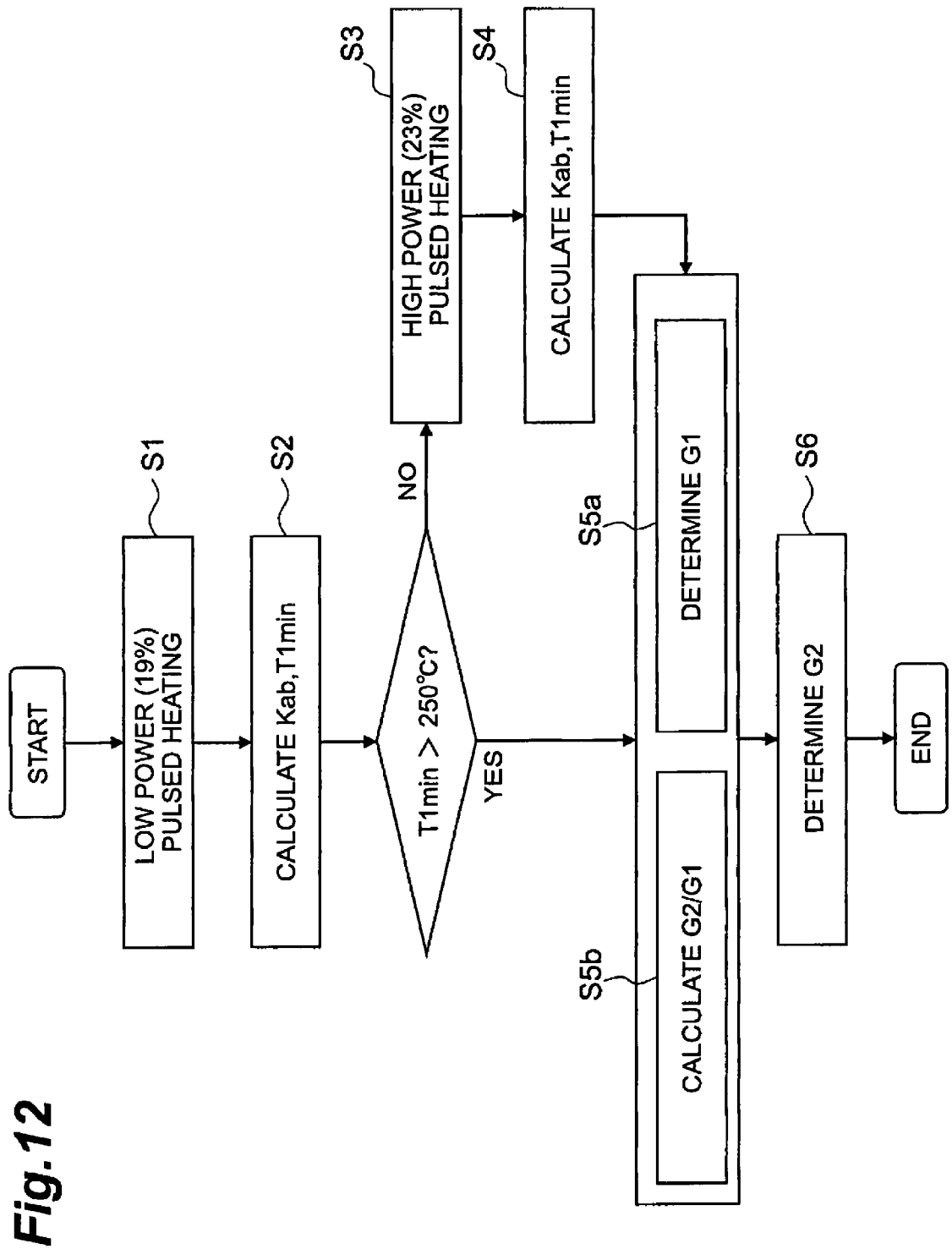
FIG. 12 A flowchart showing an example of method of determining a thermal process condition in accordance with an embodiment.

FIG. 12 is a flowchart showing an example of thermal process condition determining method in accordance with this embodiment. First, while the lamp power of the lamps 9 is set to 19% (low power) of the full power, for example, in the rapid thermal processing apparatus 1, a wafer is subjected to pulsed heating (step S1). At this time, the absorption correction coefficient Kab and minimum value T1min are calculated from the temperature data sequentially outputted from the temperature sensor T1 (step S2). When the minimum value T1min does not exceed the detection limit value of the temperature sensor T1, e.g., 250° C., the wafer is subjected to pulsed heating with the lamp power of the lamps 9 being set to 23% (high power) of the full power, for example (step S3). The absorption correction coefficient Kab and minimum value T1min are calculated from the temperature data obtained at this time (step S4).

Subsequently, using thus obtained (Kab)·(T1min) and the approximate lines L10, L15, L20, L25, L30, L35, L40 shown in the graph of FIG. 8, for example, the center lamp power G1 is determined (step S5a). On the other hand, using the obtained (Kab)·(T1min) and the solid line LE in FIG. 11(A) or the solid line HE in FIG. 11(B), the ratio G2/G1 is calculated (step S5b). Thereafter, using the center lamp power G1 and the ratio G2/G1, the peripheral lamp power G2 is determined (step S6).

Preferably, the pulse width in pulsed heating is at least 1 second. In this case, the wafer can be heated in a short time by pulsed heating. Consequently, the thermal property of the wafer can be determined easily in a short time, and the lamp power of the open-loop step L1 can be determined. Preferably, the pulse width is 10 seconds or less. This can restrain the wafer from drastically raising its temperature, and thus can suppress the warpage, breakage, and the like of the wafer. In an example, the pulse width can be set to 4 seconds, for example. The pulse width corresponds to the heating span HS in FIG. 7.

Second Embodiment

The substrate thermal property determining method and thermal process condition determining method in accordance with a second embodiment will now be explained. The substrate thermal property determining method in accordance with this embodiment is preferably carried out by using the rapid thermal processing apparatus 1. The thermal process condition determining method in accordance with this embodiment is preferably carried out by using the rapid thermal processing apparatus 1 prior to a rapid thermal process including the above-mentioned open-loop step L1 and closed-loop step L2.

Figure 13:
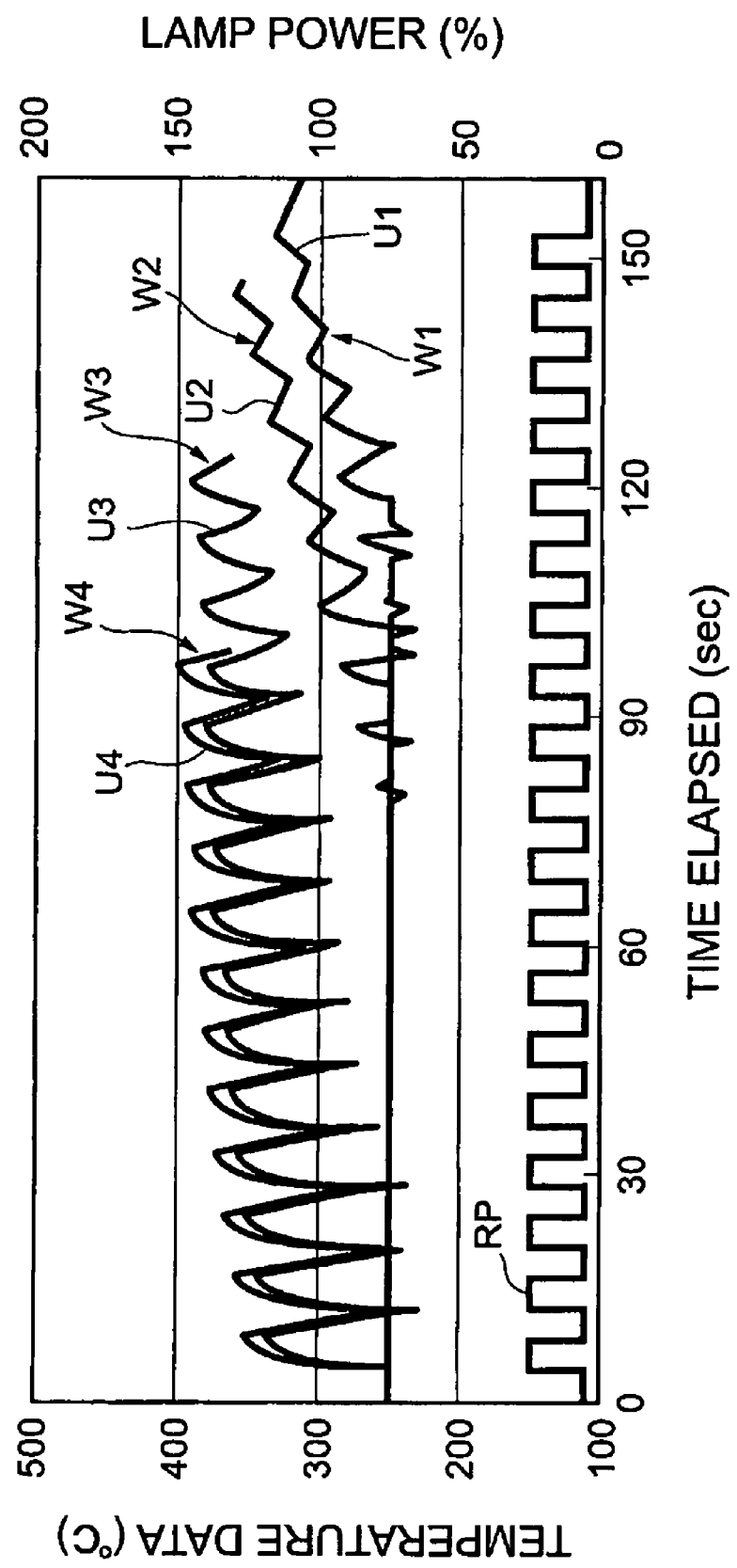
FIG. 13 A graph showing an example of temperature data sequentially outputted from a temperature sensor when wafers having thermal properties different from each other are subjected to pulsed heating.

FIG. 13 is a graph showing an example of temperature data sequentially outputted from the temperature sensor T1 when wafers W1 to W4 having thermal properties different from each other are subjected to pulsed heating. In FIG. 13, one ordinate of the graph indicates the temperature data (° C.) sequentially outputted from the temperature sensor T1, whereas the other ordinate represents the lamp power (%) in the case where the full power of the lamps 9 is 100%. The abscissa of the graph shows the time elapsed (sec). In the example shown in FIG. 13, the lamps 9 within the center region $a_1$ and region $a_2$ of the lamp group 9G each have a lamp power which is 24% of the full power, for instance, whereas the lamps 9 within the peripheral edge region $a_3$ each have a lamp power which is 5% of the full power, for instance. The pulse width is 4 seconds, for example. The other conditions at the time of pulsed heating are a pressure of 10×133.322 Pa (10 Torr) and an $N_2$ gas flow rate of 10 slm.

Waveforms U1 to U4 in the graph show data in the respective cases using the wafers W1 to W4. The wafer W1 is an Si wafer provided with an $SiO_2$ film having a thickness of 9 nm, exhibiting a radiant emissivity E of 0.60. The wafer W2 is an Si wafer provided with an $SiO_2$ film having a thickness of 170 nm, exhibiting a radiant emissivity E of 0.90. The wafer W3 is an Si wafer provided with an $S_3N_4$ film having a thickness of 240 nm, exhibiting a radiant emissivity E of 0.66. The wafer W4 is an Si wafer provided with an $S_3N_4$ film having a thickness of 120 nm, exhibiting a radiant emissivity E of 0.98. Waveform RP in the graph shows changes in lamp power with time, illustrating a waveform in which a plurality of pulses are repeated.

The graph shown in FIG. 13 indicates that the wafers W1, W2 are harder to warm while the wafers W3, W4 are easier to warm. It also indicates that the Si wafers provided with films made of the same material become easier to warm as their emissivity is higher. It further indicates that the Si wafers provided with the $S_3N_4$ films are easier to warm than those provided with the $SiO_2$ films.

Figure 14:
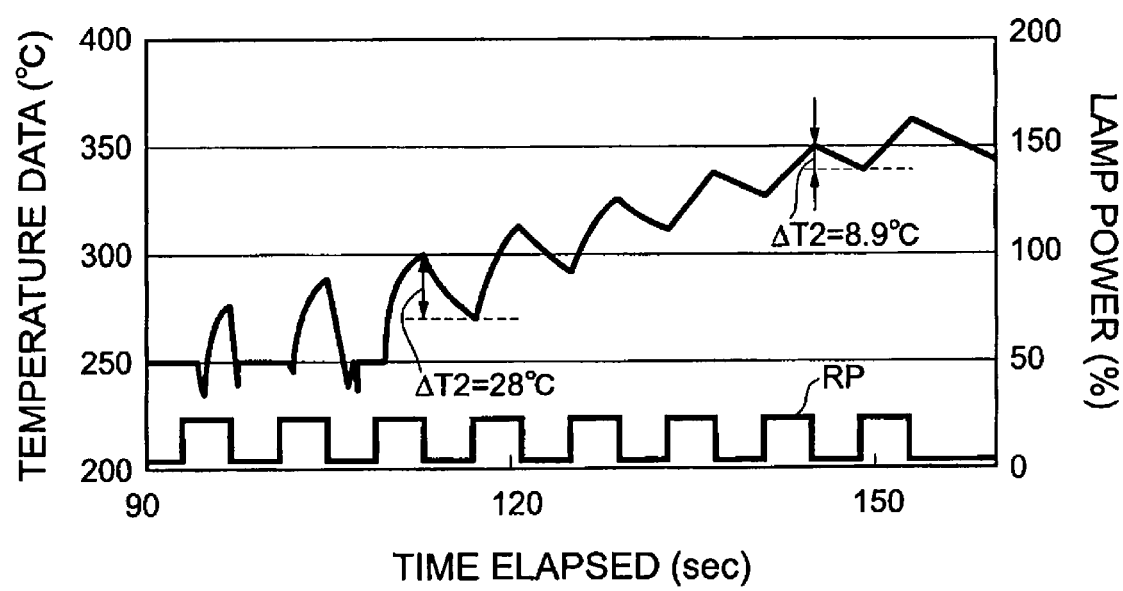
FIG. 14 A graph showing an example of temperature data sequentially outputted from the temperature sensor when a bare silicon wafer is subjected to pulsed heating.

FIG. 14 is a graph showing an example of temperature data sequentially outputted from the temperature sensor T1 when a bare silicon wafer is subjected to pulsed heating. The difference ΔT2 between adjacent local maximum and minimum in temperature data in the case where the temperature data is 300° C. or less, is greater than that in the case where temperature data exceeds 300° C. This indicates that the energy ray transmitted through the wafer is more influential in the case where the temperature data is 300° C. or less.

Using the temperature data shown in FIGS. 13 and 14 can determine thermal properties of wafers easily in a short time. Also, the lamp power in the open-loop step can be determined easily in a short time as in the first embodiment. This lamp power indicates the lamp power of the lamps 9 within the center region $a_1$ and region $a_2$ of the lamp group 9G shown in FIG. 5, for example. The lamp power of the lamps 9 within the center region $a_1$ and the lamp power of the lamps 9 within the region $a_2$ may be either the same or different from each other. Further, the use of pulsed heating makes it possible to heat the wafer in a short time while fully suppressing the warpage, breakage, and the like thereof.

FIG. 15(A) is a chart showing relationships between the center lamp power G1 and peripheral lamp power G2 concerning wafers W5 to W9 having thermal properties different from each other. FIG. 15(A) lists the peripheral edge lamp power G2 minimizing the in-plane temperature difference ΔT for each central lamp power G1. FIG. 15(B) is a graph showing the ratio G2/G1 for the wafers W5 to W9. FIGS. 15(A) and 15(B) verify that the ratio G2/G1 is a characteristic value of each wafer.

Figure 16:
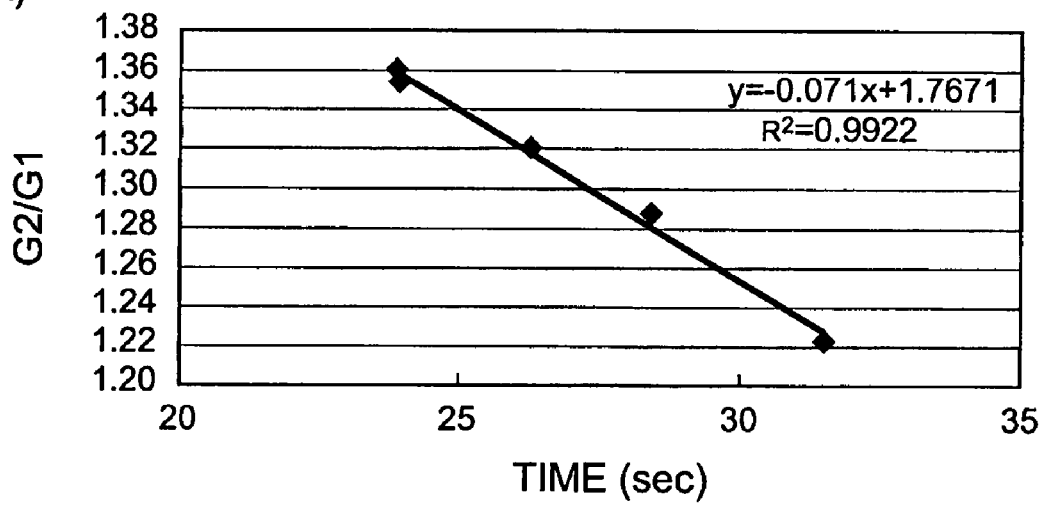
Figure 16:
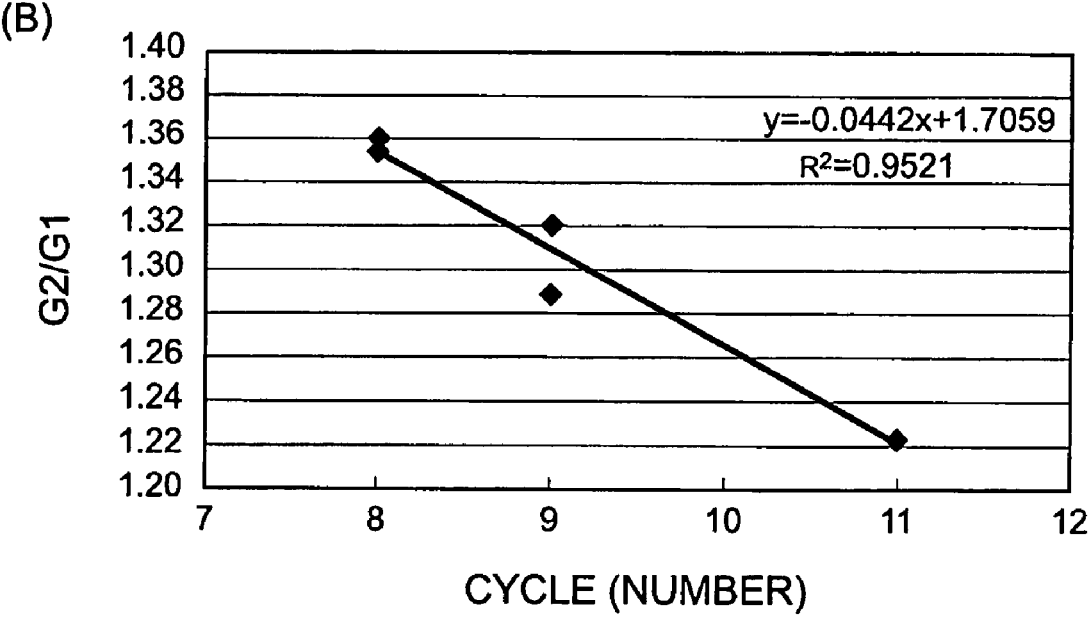

FIG. 16(A) is a graph showing the relationship between the time required for raising the temperature data obtained from the temperature sensor 1 from 250° C. to 380° C. and the ratio G2/G1 when wafers W5 to W9 are subjected to continuous heating. In this continuous heating, the lamp power of the lamps 9 within the center region $a_1$ and region $a_2$ of the lamp group 9G shown in FIG. 5 is set to 20% of the full power. Using FIG. 16(A), the ratio G2/G1 of a wafer can be calculated from the time required for the temperature data obtained from the temperature sensor T1 to rise from 250° C. to 380° C. when the wafer is subjected to continuous heating.

FIG. 16(B) is a graph showing the relationship between the cycle (number) of pulses required for the temperature data obtained from the temperature sensor T1 to reach a predetermined temperature and the ratio G2/G1 when the wafers W5 to W9 are subjected to pulsed heating. In the heating periods of this pulsed heating process, the lamp power of the lamps 9 within the center region $a_1$ and region $a_2$ of the lamp group 9G shown in FIG. 5 is set to 20% of the full power. Using FIG. 16(B), the ratio G2/G1 of a wafer can be calculated from the cycles of pulses required for the temperature data obtained from the temperature sensor T1 to reach a predetermined temperature when the wafer is subjected to pulsed heating.

Though preferred embodiments of the present invention are explained in detail in the foregoing, the present invention is not limited to the above-mentioned embodiments.

For example, the ratio G2/G1 may be calculated before or after determining the center lamp power G1. The determination of the center lamp power and the calculation of the ratio G2/G1 may be done at the same time.

INDUSTRIAL APPLICABILITY

The present invention is employable in uses which can determine a thermal property of a substrate in a short time and can determine a thermal process condition of an open-loop step.

The invention claimed is:

1. A substrate thermal property determining method comprising the steps of:
obtaining, in a rapid thermal processing apparatus comprising a lamp for heating a substrate and a temperature sensor arranged so as to oppose the lamp, temperature data sequentially outputted from the temperature sensor while subjecting the substrate arranged between the lamp and the temperature sensor to heating with a plurality of pulses from the lamp; and
determining a thermal property of the substrate by using maximum and minimum values of the temperature data in a measurement period of the temperature data.

2. A substrate thermal property determining method according to claim 1, wherein a pulse width of each pulse in the plurality is 10 seconds or less.

3. The substrate thermal property determining method according to claim 1, wherein the thermal property of the substrate is at least one of an infrared absorption characteristic or an infrared transmission characteristic.

4. A substrate thermal property determining method according to claim 1, wherein a pulse width of each pulse in the plurality is at least 1 second.

5. A substrate thermal property determining method according to claim 4, wherein a pulse width of each pulse in the plurality is at least 1 second and 10 seconds or less.

6. A thermal process condition determining method of determining, in a rapid thermal processing apparatus comprising a lamp for heating a substrate and a temperature sensor arranged so as to oppose the lamp, a thermal process condition of an open-loop step for raising a temperature of the substrate arranged between the lamp and the temperature sensor under open-loop control, the method comprising the steps of:
obtaining temperature data sequentially outputted from the temperature sensor while subjecting the substrate to heating with a plurality of pulses from the lamp in the rapid thermal processing apparatus; and
determining the thermal process condition of the open-loop step by using maximum and minimum values of the temperature data in a measurement period of the temperature data.

7. A thermal process condition determining method according to claim 6, wherein a pulse width of each pulse in the plurality is 10 seconds or less.

8. A thermal process condition determining method according to claim 6, wherein a pulse width of each pulse in the plurality is at least 1 second.

9. A thermal process condition determining method according to claim 8, wherein a pulse width of each pulse in the plurality is at least 1 second and 10 seconds or less.

10. A thermal process condition determining method of determining, in a rapid thermal processing apparatus comprising a lamp for heating a substrate and a temperature sensor arranged so as to oppose the lamp, a thermal process condition of an open-loop step for raising a temperature of the substrate arranged between the lamp and the temperature sensor under open-loop control, the method comprising the steps of:
obtaining temperature data sequentially outputted from the temperature sensor while subjecting the substrate to heating with a plurality of pulses from the lamp in the rapid thermal processing apparatus; and
determining the thermal process condition of the open-loop step by using the temperature data, wherein the thermal process condition of the open-loop step includes a first thermal process condition for raising a temperature of a first region including a center part of the substrate and a second thermal process condition for raising a temperature of a second region of the substrate surrounding the center part of the substrate and having a thermal property different from that of the first region; and
wherein the step of determining the thermal process condition of the open-loop step comprises:

determining the first thermal process condition by using the temperature data;

calculating a ratio of the second thermal process condition to first thermal process condition by using the temperature data; and determining the second thermal process condition by using the first thermal process condition and the ratio.

11. A thermal process condition determining method according to claim 10, wherein the step of determining the first thermal process condition determines the first thermal process condition by using maximum and minimum values of the temperature data in a measurement period of the temperature data; and wherein the step of calculating the ratio calculates the ratio by using the maximum and minimum values of the temperature data in the measurement period of the temperature data.

12. A thermal process condition determining method according to claim 10, wherein a pulse width of each pulse in the plurality is at least 1 second.

13. A thermal process condition determining method according to claim 12, wherein the step of determining the first thermal process condition determines the first thermal process condition by using maximum and minimum values of the temperature data in a measurement period of the temperature data; and wherein the step of calculating the ratio calculates the ratio by using the maximum and minimum values of the temperature data in the measurement period of the temperature data.

14. A thermal process condition determining method according to claim 10, wherein a pulse width of each pulse in the plurality is 10 seconds or less.

15. A thermal process condition determining method according to claim 14, wherein the step of determining the first thermal process condition determines the first thermal process condition by using maximum and minimum values of the temperature data in a measurement period of the temperature data; and wherein the step of calculating the ratio calculates the ratio by using the maximum and minimum values of the temperature data in the measurement period of the temperature data.

16. A thermal process condition determining method according to claim 10, wherein a pulse width of each pulse in the plurality is at least 1 second and 10 seconds or less.

17. A thermal process condition determining method according to claim 16, wherein the step of determining the first thermal process condition determines the first thermal process condition by using maximum and minimum values of the temperature data in a measurement period of the temperature data; and wherein the step of calculating the ratio calculates the ratio by using the maximum and minimum values of the temperature data in the measurement period of the temperature data.

* * * * *